(12) United States Patent
Chen et al.

(10) Patent No.: US 10,456,428 B2
(45) Date of Patent: Oct. 29, 2019

(54) METHOD OF TREATING PSORIASIS

(71) Applicant: GENMONT BIOTECH INC., Tainan (TW)

(72) Inventors: Yi-Hsing Chen, Tainan (TW); Wan-Hua Tsai, Kaohsiung (TW); Chia-Hsuan Chou, Tainan (TW); Pei-Jane Tsai, Tainan (TW); Tsuei Yin Huang, Tainan (TW)

(73) Assignee: GENMONT BIOTECH INC., Tainan (TW)

( * ) Notice: Subject to any disclaimer, the term of this patent is extended or adjusted under 35 U.S.C. 154(b) by 7 days.

(21) Appl. No.: 15/675,809

(22) Filed: Aug. 14, 2017

(65) Prior Publication Data
US 2018/0256651 A1 Sep. 13, 2018

(30) Foreign Application Priority Data
Mar. 7, 2017 (TW) .............................. 106107470 A

(51) Int. Cl.
*A61K 35/74* (2015.01)
*A61K 35/00* (2006.01)

(52) U.S. Cl.
CPC .......... *A61K 35/74* (2013.01); *A61K 2035/11* (2013.01)

(58) Field of Classification Search
CPC .... A23L 33/00; A23L 27/204; A23L 27/2054; A23L 27/2056; A23L 27/86; A23L 33/135; A23L 33/195; A61K 2035/11; A61K 35/74; A61K 35/747; A61K 2035/115; A61K 31/7004; A61K 31/7016; A61K 31/715; A61K 35/39; A61K 35/741; A61K 35/742; A61K 35/744; A61K 35/745; A61K 38/46; A61K 9/0031; A61K 9/0053; A61K 9/19; A61K 47/22; A61K 2039/505; A61K 31/7105; A61K 35/15; A61K 35/17; A61K 39/0011; A61K 39/3955; A61K 31/19; A61K 31/198; A61K 38/20; A61K 38/2013; A61K 38/2066; A61K 38/26; A61K 38/446; A61K 47/6901; A61K 9/0024; A61K 39/00; A61K 9/1647; A61K 9/1652; A61K 9/1658; A61K 9/1611; A61K 47/10; A61K 9/50; A61K 38/164; A61K 39/02; A61K 36/48; A61K 38/018; Y02A 50/414; Y02A 50/401; Y02A 50/473; Y02A 50/411; Y02A 90/26; C07D 413/14; A61P 35/00; A61P 37/00; A61P 25/28; A61P 3/10; A23V 2002/00; A23V 2200/318; A23V 2200/3202; A23V 2200/3204; A23V 2200/31; C12N 15/70; C12N 9/001; C12N 9/1217; C12N 1/36; C12N 9/88; C12Y 103/08001; C12Y 115/01001; C12Y 207/02007; A23Y 2220/63; A23Y 2220/43; A23Y 2220/67; A23P 10/30; C07K 14/195; C07K 14/335; C07K 14/435; C07K 14/575; C07K 2319/00; C07K 2319/036; B33Y 80/00; G01N 33/48; G06F 19/3468; C12R 1/225; C12R 1/25; A01N 63/00; A61L 2300/258; A61L 27/54; A61L 31/16
See application file for complete search history.

(56) References Cited

U.S. PATENT DOCUMENTS

2016/0067289 A1* 3/2016 Berggren ............. A61K 35/747
424/93.45

OTHER PUBLICATIONS

Ichiwara et al., Biosci. Biotechnol. Biochem., 73 (7), 1561-1565, 2009.*
Benyacoub et al., Beneficial Microbes, 2014; 5(2): 129-136.*
Gueniche et al., Beneficial Microbes, 2014; 5(2): 137-145.*

* cited by examiner

*Primary Examiner* — Deborah K Ware
(74) *Attorney, Agent, or Firm* — Soroker Agmon Nordman

(57) ABSTRACT

A method and a composition having the *Lactobacillus paracasei* strain GMNL-653 for treating psoriasis is provided. The *Lactobacillus paracasei* strain GMNL-653 has anti-inflammation properties, and inhibits the secretion of cytokine IL-6 and IL-17, so that the psoriasis symptoms caused by over-inflammation are improved/relieved.

3 Claims, 9 Drawing Sheets
Specification includes a Sequence Listing.

METHOD OF TREATING PSORIASIS

CROSS REFERENCE TO RELATED APPLICATIONS

This application claims the benefit of the filing date of Taiwan patent application No. 106107470, filed on Mar. 7, 2017, the disclosure of which is incorporated herein by reference.

FIELD OF THE INVENTION

The present invention relates to a *Lactobacillus paracasei* strain and a composition thereof for improving psoriasis, and in particular relates to a *Lactobacillus paracasei* strain GMNL-653 and a composition including the *Lactobacillus paracasei* strain GMNL-653 which has an anti-inflammatory ability and is capable of inhibiting cytokines IL-6 and IL-17 secretion.

BACKGROUND OF THE INVENTION

Psoriasis is a chronic immune disease that is recurrent. Due to the skin's immune system disorder, the increased skin cells form a thick dander. The red desquamation plaque easily regrows on the scalp, face, body, and limbs of patients, and most of the patients cannot be cured all their life. Some patients with psoriasis will also have psoriatic arthritis, causing joint inflammation and swelling. The psoriasis is not only a skin disease, but also a systemic disease. 40% of patients have arthritis, and they have a higher chance of having hyperlipidemia, metabolic syndrome, obesity, cardiovascular disease, diabetes, or depression than a normal person.

The most commonly used method for the treatment of psoriasis is the use of topical medications, oral drugs, biological agents, and light therapy. Common topical medications contain: (1) Topical steroids, which are anti-inflammatory, and can inhibit cell proliferation. However, with long-term use on the thin skin, they will cause side effects such as skin atrophy; (2) Vitamin D can inhibit keratinocyte proliferation, and is anti-inflammatory, but there will be local irritation; (3) Topical retinoic acid can inhibit excessive keratinocytes, and promote keratinocyte differentiation, but the effect is poor; (4) Tar can help anti-inflammation and inhibit keratinocyte hyperplasia; (5) Moisturizers can prevent the skin from being too dry and stimulating inflammation. The oral drugs include: (1) MTX (methotrexate) has the main side effects of blood cell reduction and liver toxicity; and (2) Cyclosporine has the main side effects of blood cell reduction and renal toxicity; (3) Isotretinoin has the main side effects of abnormal liver function, elevated blood lipids, dry skin, and teratogenic embryos; (4) Systemic steroids are only given to pregnant women. Biological agents are injectable antibodies with immuno-regulatory functions. They are safe, but expensive, and the user must watch for tuberculosis. The time period of the light therapy should be evaluated and decided on by the physician, and the patient must go to the hospital.

The above-mentioned treatments of psoriasis generally have the disadvantages of high side effects, poor convenience, and high cost. Therefore, looking for non-steroidal treatments which are convenient and inexpensive will become a new trend in the future treatment of psoriasis.

It is therefore necessary to provide a composition having a *Lactobacillus paracasei* strain GMNL-653 for treating psoriasis, in order to solve the problems existing in the conventional technology as described above.

SUMMARY OF THE INVENTION

A primary object of the present invention is to provide a *Lactobacillus paracasei* strain GMNL-653 and a composition thereof for improving psoriasis symptoms. The *Lactobacillus paracasei* strain GMNL-653 has an anti-inflammatory ability, and can inhibit and reduce the contents of cytokine IL-6 and IL-17 in serum, so as to improve/relieve psoriasis symptoms.

To achieve the above objects, the present invention provides a composition for treating psoriasis, comprising *Lactobacillus paracasei* strain GMNL-653 deposited in the China Center for Type Culture Collection (CCTCC) with an accession number of CCTCC M2016226.

In one embodiment of the present invention, the *Lactobacillus paracasei* strain GMNL-653 is a viable strain or a dead strain.

In one embodiment of the present invention, the *Lactobacillus paracasei* strain GMNL-653 has the ability to inhibit the formation of cytokine IL-17.

In one embodiment of the present invention, the *Lactobacillus paracasei* strain GMNL-653 has the ability to inhibit the formation of cytokine IL-6.

In one embodiment of the present invention, the composition is a pharmaceutical composition, a nutritional supplement, a health food, a medical food, or the combination thereof.

DETAILED DESCRIPTION OF THE PREFERRED EMBODIMENTS

Figure 1:
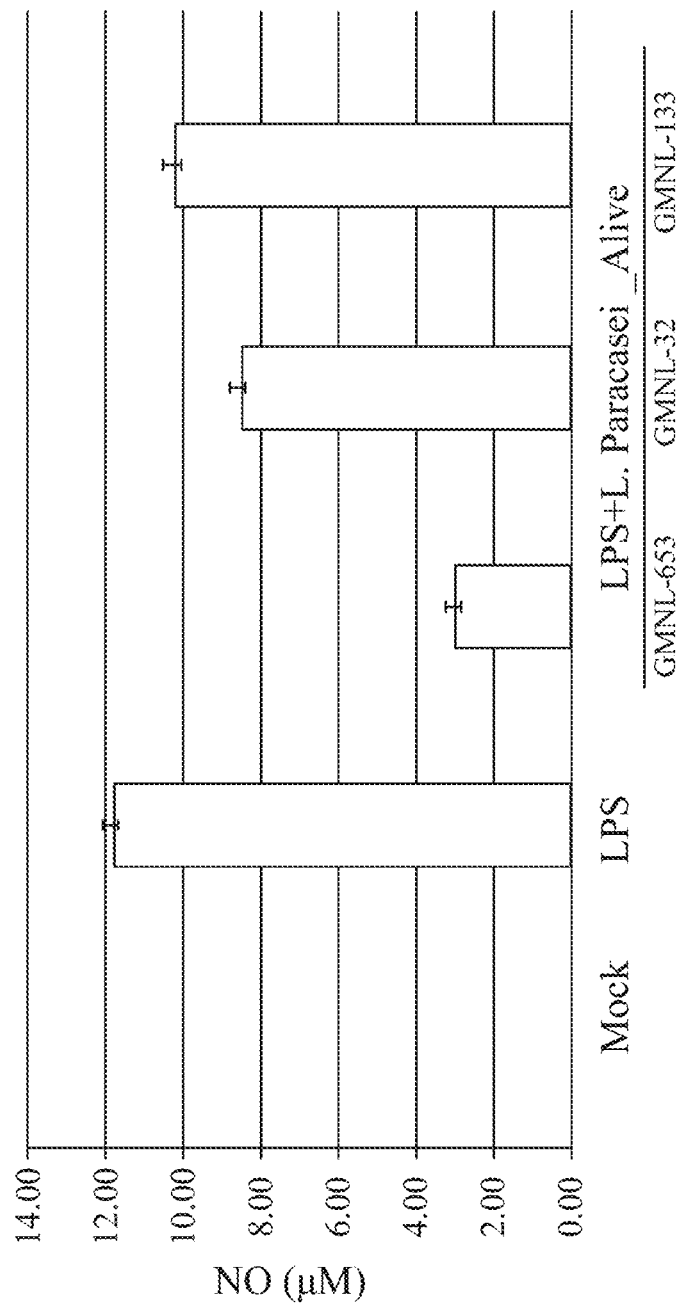
FIG. 1 is a diagram showing the effect of different *Lactobacillus paracasei* strains (viable strains GMNL-653, GMNL-32, and GMNL-133) on NO content in the anti-inflammatory test of the experiment 1.

The structure and the technical means adopted by the present invention to achieve the above and other objects can be best understood by referring to the following detailed description of the preferred embodiments. Furthermore, if there is no specific description in the invention, singular terms such as "a", "one", and "the" include the plural number. For example, "a compound" or "at least one compound" may include a plurality of compounds, and the mixtures thereof. If there is no specific description in the invention, "%" means "weight percentage (wt %)", and the numerical range (e.g., 10%-11% of A) contains the upper and lower limit (i.e., 10%≤A≤11%). If the lower limit is not defined in the range (e.g., less than, or below 0.2% of B), it means that the lower limit may be 0 (i.e., 0%≤B≤0.2%). The proportion of "weight percent" of each component can be replaced by the proportion of "weight portion" thereof. The abovementioned terms are used to describe and understand the present invention, but the present invention is not limited thereto.

One embodiment of the present invention provides a *Lactobacillus paracasei* strain for improving/relieving psoriasis. The *Lactobacillus paracasei* strain is referred to as *Lactobacillus paracasei* strain GMNL-653, which is deposited in the China Center for Type Culture Collection (CCTCC) with an accession number of CCTCC M2016226.

One embodiment of the present invention provides a composition for improving/relieving psoriasis, comprising the abovementioned *Lactobacillus paracasei* strain GMNL-653. Preferably, the composition can be a pharmaceutical composition, a nutritional supplement, a health food, a medical food, or the combination thereof. The composition can be formed in various forms based on the effectivity or convenience. In addition, the composition is preferably administrated by means of food to enter the digestive system.

The *Lactobacillus paracasei* strain GMNL-653 in the abovementioned embodiments is one of a plurality of isolates mainly isolated from human intestines. The primers (SEQ ID NO: 1 and SEQ ID NO: 2) listed in Table 1 are used to perform PCR to reproduce 16S rDNA segments of each isolate, and then sequencing the 16S rDNA segment of each isolate. After sequencing, a 16S rDNA gene sequence of one of the isolates can be obtained as below (SEQ ID NO: 3); subsequently, from the comparison results on the NCBI website, it shows that the 16S rDNA sequences of the isolates are similar to that of the *Lactobacillus paracasei* strains with identities all over 99%, so that the strain GMNL-653 indeed belongs to the *Lactobacillus paracasei* genus.

TABLE 1

| | PCR primer | |
|---|---|---|
| Primer | SEQ ID NO: | SEQ |
| PAF | 1 | AGA GTT TGA TCC TGG CTC AG |
| 536R | 2 | GTA TTA CCG CGG CTG CTG |

A complete 16S rDNA sequence (SEQ ID NO: 3) of the *Lactobacillus paracasei* strain GMNL-653 is listed as below:

CGGAGGCCCCTATGATGGGCGTCGTACGAGTTCTCGTTGA

TGATCGGTGCTTGCACCGAGATTCTCATGGAACGAGTGGCGGACGGGT

GAGTAACACGTGGGTAACCTGCCCTTAAGTGGGGGATAACATTTGGAAA

CAGATGCTAATACCGCATAGATCCTGTAACCGCATGGTTCTTGGCTGATA

GATGGCGTAAGCTATCGCTGTTGGATGGACCCGCGGCGTATTATCTAGT

TGGTGAGGTAGTGGCTCACCGAGGCCATGATACGTATCCGAGCTGAGA

GGTTGATGGGCGAGTTTGTGACTGAGACACGTCCCAAACTACTACGGGA

GGCAGCAGTAGGGAATCTTCCACAATGGACGCAAGTCTGATGGAGCAAC

GCCGCGTGAGTGAAGAAGGCTTTCGGGTCGTAAAACTCTGTTGTTGGAG

AAGAATGGTCGGCAGAGTAACTGTTGTCGGCGTGACGGTATCCAACCAG

AAAGCCACGGCTAACTACGTGCCAGCAGCCGGGGGGTAATACA

A fermentation test to the *Lactobacillus paracasei* strain GMNL-653 is carried out to obtain the results shown in Table 2.

TABLE 2

| | Fermentation Test | |
|---|---|---|
| Strips No. | carbohydrates substrate | GMNL-653 |
| 0 | CONTROL | − |
| 1 | Glycerol | − |
| 2 | Erythritol | − |
| 3 | D-Arabinose | − |
| 4 | L-Arabinose | − |
| 5 | D-Ribose | + |
| 6 | D-Xylose | − |
| 7 | L-Xylose | − |
| 8 | D-Adonitol | − |
| 9 | Methyl-β-D-Xylopyranoside | − |
| 10 | D-Galactose | + |
| 11 | D-Glucose | + |
| 12 | D-Fructose | + |
| 13 | D-Mannose | + |
| 14 | L-Sorbose | − |
| 15 | L-Rhamnose | − |
| 16 | Dulcitol | − |
| 17 | Inositol | + |
| 18 | D-Mannitol | + |
| 19 | D-Sorbitol | − |
| 20 | Methyl-α-D-mannopyranoside | − |
| 21 | Methyl-α-D-glucopyranoside | + |
| 22 | N-Acetyl glucosamine | + |
| 23 | Amygdalin | − |
| 24 | Arbutin | + |
| 25 | Esculin ferric citrate | + |
| 26 | Salicin | + |
| 27 | D-Cellobiose | + |
| 28 | D-Maltose | + |
| 29 | D-Lactose (bovine origin) | − |
| 30 | D-Melibiose | − |
| 31 | D-Saccharose (sucrose) | + |
| 32 | D-Trehalose | + |
| 33 | Inulin | − |
| 34 | D-Melezitose | + |
| 35 | D-Raffinose | − |
| 36 | Amidon (starch) | − |
| 37 | Glycogen | − |
| 38 | Xylitol | − |
| 39 | Gentiobiose | − |
| 40 | D-Turanose | + |
| 41 | D-Lyxose | − |
| 42 | D-Tagatose | + |
| 43 | D-Fucose | − |
| 44 | L-Fucose | − |
| 45 | D-Arabitol | − |
| 46 | L-Arabitol | − |
| 47 | Potassium gluconate | − |
| 48 | Potassium 2-ketogluconate | − |
| 49 | Potassium 5-ketogluconate | − |

−: negative;
+: positive

To verify the anti-inflammatory properties of the *Lactobacillus paracasei* strain GMNL-653 according to the present invention, and to confirm that the psoriasis can be improved/relieved, experiments 1 to 3 are executed. In the animal model, the mouse has symptoms closer to human diseases including chronic skin irritation and keratosis. Therefore, the mouse model is useful for evaluating and simulating the effects when the *Lactobacillus paracasei* strain GMNL-653 is applied to a human.

Experiment 1: Anti-Inflammatory Test

*Lactobacillus paracasei* strains: GMNL-653 being provided by one embodiment of the present invention; GMNL-32 and GMNL-133 being comparison groups.

Bacteria Broth Culture:

Inoculating the *Lactobacillus paracasei* GMNL-653 from a frozen tube to 1 ml of MRS broth, and standing under 37° C. for aerobically incubating for 20 hours. The next day, adding 15 μl culture solution into 1.5 ml of MRS broth (1% secondary activation), and then standing under 37° C. for aerobically incubating for 20 hours.

Cell Culture:

Adjusting the cell number of macrophage cells (RAW 264.7) to $8 \times 10^5$ cells/ml. Adding 0.5 ml of cell solution (with a final cell number of $4 \times 10^5$ cells/well) into a 24-well plate, and standing at 37° C. overnight. Next, using phosphate buffer saline (called PBS hereinafter) to clean the 24-well plate one time, and then replacing the culture medium with 0.4 ml/well culture medium without serum (DMEM) to execute starvation for 2 hours.

Co-Culture of Bacteria and Cell:

Taking the bacteria solution, which was incubated the previous night, to centrifuge for 1 minute (13000 rpm), and carrying out PBS washing twice. After removing the supernatant again, having 20 μl of PBS suspension of bacteria to mix with 980 μl of PBS (dilute 50 fold). Measuring OD 600, estimating back to adjust the bacteria concentration to $1 \times 10^{10}$ CFU/ml. Having 0.1 ml of the adjusted bacterial solution to mix with 0.9 ml of DMEM (without serum), so that the final number of the bacteria comes to $1 \times 10^9$ CFU/ml. Repeating the above steps to prepare two tubes of the final number of the bacteria. One tube is for viable bacteria and another tube is for dead bacteria which is prepared by thermal killing (at 121° C. for 15 mins). After cell starvation is executed for 2 hours, respectively adding 100 μl of the viable and dead bacteria solutions (with final bacteria concentration of $1 \times 10^8$ CFU/ml) for treating the cells for 2 hours.

Continuously adding 0.5 ml DMEM, including 200 ng/ml of LPS, into each hole after the co-culture of the bacteria solution and the cells are executed for 2 hours; and the control group (mock) is provided by adding 0.5 ml DMEM. Culturing together again for 20 hours, collecting the supernatant for measuring NO (nitric oxide) content of each group.

Mixing NO reagent (80 μl Griess reagent A+80 μl Griess reagent B) with 80 μl cell supernatant to react together under room temperature for 5 minutes. Next, using an ELISA reader to determine absorbance value of OD 550 nm.

Figure 2:
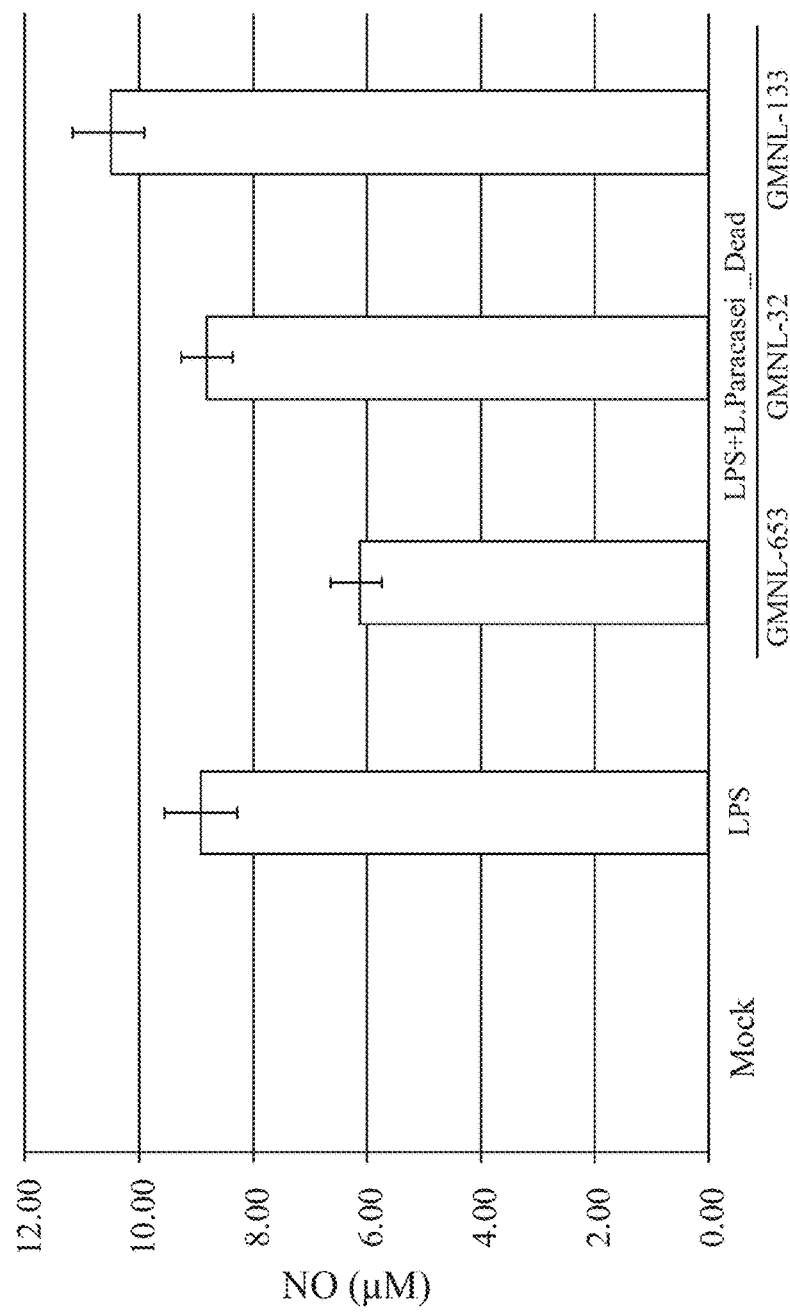
FIG. 2 is a diagram showing the effect of different *Lactobacillus paracasei* strains (dead strains GMNL-653, GMNL-32, and GMNL-133) on NO (nitric oxide) content in the anti-inflammatory test of the experiment 1.

The results are shown in FIGS. 1-2. It can be found that LPS can effectively promote the generation of NO which is the inflammatory substance of RAW264.7 cells. In FIG. 1, three *Lactobacillus paracasei* viable strains (GMNL-653, 32, and 133) can reduce the NO concentration, and the GMNL-653 has best effect. In FIG. 2, it can be found that only the strain GMNL-653 can reduce the NO concentration, the other two have a non-obvious effect on the NO concentration, even the strain GMNL-133 makes the NO concentration raise slightly. Therefore, it can be understood that the viable or dead strain of the *Lactobacillus paracasei* strain GMNL-653 both can effectively inhibit the inflammation caused by the LPS-stimulated RAW264.7 cell. The *Lactobacillus paracasei* strain GMNL-653 has an anti-inflammatory ability.

Experiment 2: Different Dosages of the
*Lactobacillus paracasei* Strain GMNL-653 for
Inhibiting Cytokine IL-6 Generated During
Inflammations Bacteria Broth Culture:

Inoculating the *Lactobacillus paracasei* strain GMNL-653 from a frozen tube to 1 ml of MRS broth, and standing under 37° C. for aerobically incubating for 20 hours. The next day, adding 15 μl culture solution into 1.5 ml of MRS broth (1% secondary activation), and then standing under 37° C. for aerobically incubating for 20 hours.

Cell Culture:

Adjusting the cell number of macrophage cells (RAW 264.7) to $8 \times 10^5$ cells/ml. Adding 0.5 ml of cell solution (with a final cell number of $4 \times 10^5$ cells/well) into a 24-well plate, and standing at 37° C. overnight. Next, using PBS to clean the 24-well plate one time, and then replacing the culture medium with 0.4 ml/well culture medium without serum (DMEM) to execute starvation for 2 hours.

Co-Culture of Bacteria and Cell:

Taking the bacteria solution, which was incubated the previous night, to centrifuge for 1 minute (13000 rpm), and carrying out PBS washing twice. After removing the supernatant again, having 20 μl of PBS suspension of bacteria to mix with 980 μl of PBS (dilute 50 fold). Measuring OD 600, estimating back to adjust the bacteria concentration to $1 \times 10^{10}$ CFU/ml. Having 0.2 ml of the adjusted bacterial solution to mix with 0.8 ml of DMEM (without serum), so that the final number of the bacteria comes to $2 \times 10^9$ CFU/ml. The final concentration was previously adjusted in the sequence of $2 \times 10^9$, $1 \times 10^9$, $5 \times 10^8$, $1 \times 10^8$, $5 \times 10^7$ CFU/ml. After cell starvation is executed for 2 hours, adding 100 μl of the bacteria solutions having different diluting folds for treating the cells for 2 hours.

Figure 3:
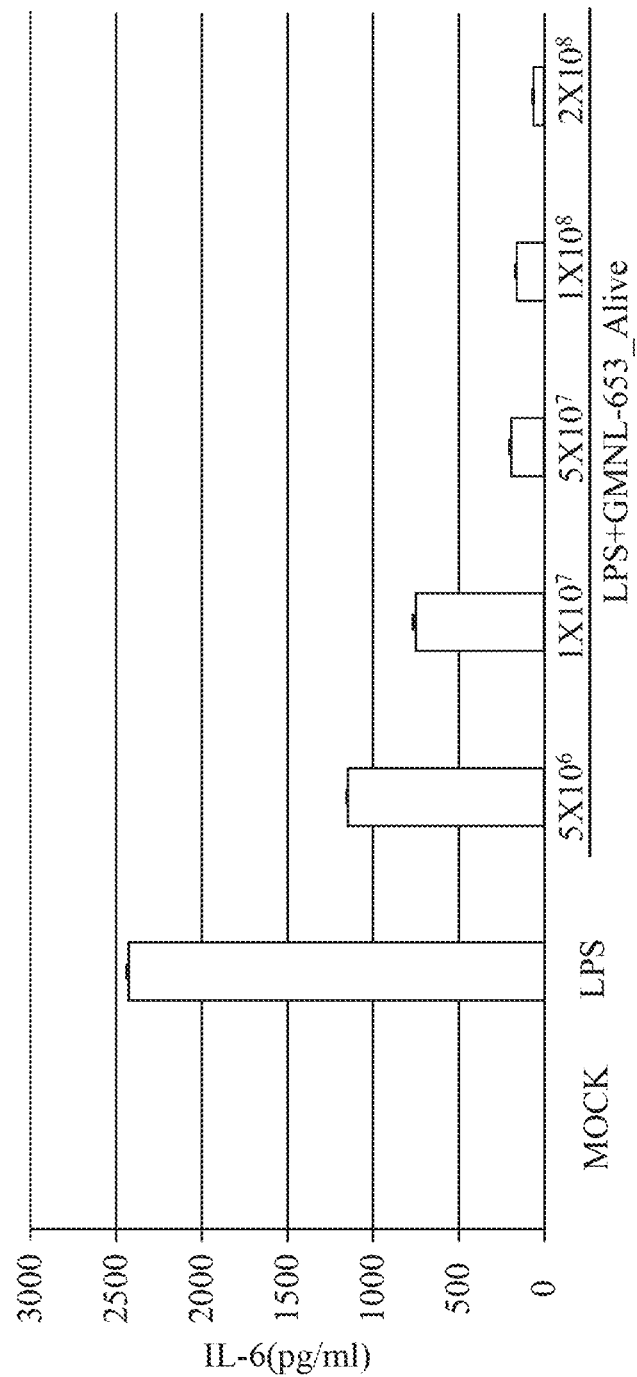
FIG. 3 is a diagram showing the expression of cytokine IL-6 of each group in the experiment 2 according to one embodiment of the present invention.

Referring to FIG. 3 for the results of the experiment 2, it can be seen that all of the different dosages of the *Lactobacillus paracasei* strain GMNL-653 can reduce the cytokine IL-6 secretion generated by the LPS-stimulated RAW264.7. The higher dosage, the better the inhibition of the cytokine secretion.

Experiment 3: Psoriasis Mouse Model

Material: 10-week-old BALB/c female rats were divided into four groups, including a control group (fed with sterile water, had no disease model, 2 rats), a disease group (fed with sterile water, had the disease model, 5 rats), and a *Lactobacillus paracasei* group (had the disease model; fed with viable bacteria having a dose of $1.6 \times 10^7$ cfu/mouse, 5 rats; and fed with dead bacteria having a dose of $8.1 \times 10^7$ cells/mouse, 5 rats).

Analysis Method:

(1) Viable bacteria preparation: Inoculating the *Lactobacillus paracasei* GMNL-653 from a frozen tube to 1 ml of MRS broth, and standing under 37° C. for aerobically incubating for 20 hours. The next day, adding 15 μl culture solution into 1.5 ml of MRS broth (1% secondary activation), and then standing under 37° C. for aerobically incubating for 20 hours. Next, measuring OD 600, and estimating back to adjust the bacteria concentration to $8 \times 10^7$ CFU/ml.

(2) Dead bacterial preparation: Inoculating the *Lactobacillus paracasei* GMNL-653 from a frozen tube to 1 ml of MRS broth, and standing under 37° C. for aerobically incubating for 20 hours. The next day, adding 15 μl culture solution into 1.5 ml of MRS broth (1% secondary activation), and then standing under 37° C. for aerobically incubating for 20 hours. Next, measuring OD 600, and estimating back to adjust the bacteria concentration to $4 \times 10^8$ CFU/ml. Using thermal killing to kill the bacteria at 121° C. for 15 minutes.

Process flow: Pipe-feeding the BALB/c mice every day with *Lactobacillus paracasei* strains; Continuously feeding for 6 days, the mouse has its back hair removal at the sixth day, and then performing disease animal model at the seventh day by applying 0.05 g Imiquimod Cream (5% Aldara, called Imq) on the skin. In the control group, Vaseline is applied on the mouse skin for 7 days and continuously feeding the *Lactobacillus paracasei* strains. Taking pictures to record the condition of the dander of the skin, and collecting the mouse serum by heart blood collection. The cytokine IL-17 analysis is carried out by ELISA kit (BioLgend, Mouse IL-17A, Cat. No. 432505). The obtained data are analyzed by means of two-way analysis of variance, and T-test to compare with the disease group (Imq). ** indicates $p<0.01$.

Figure 4A:
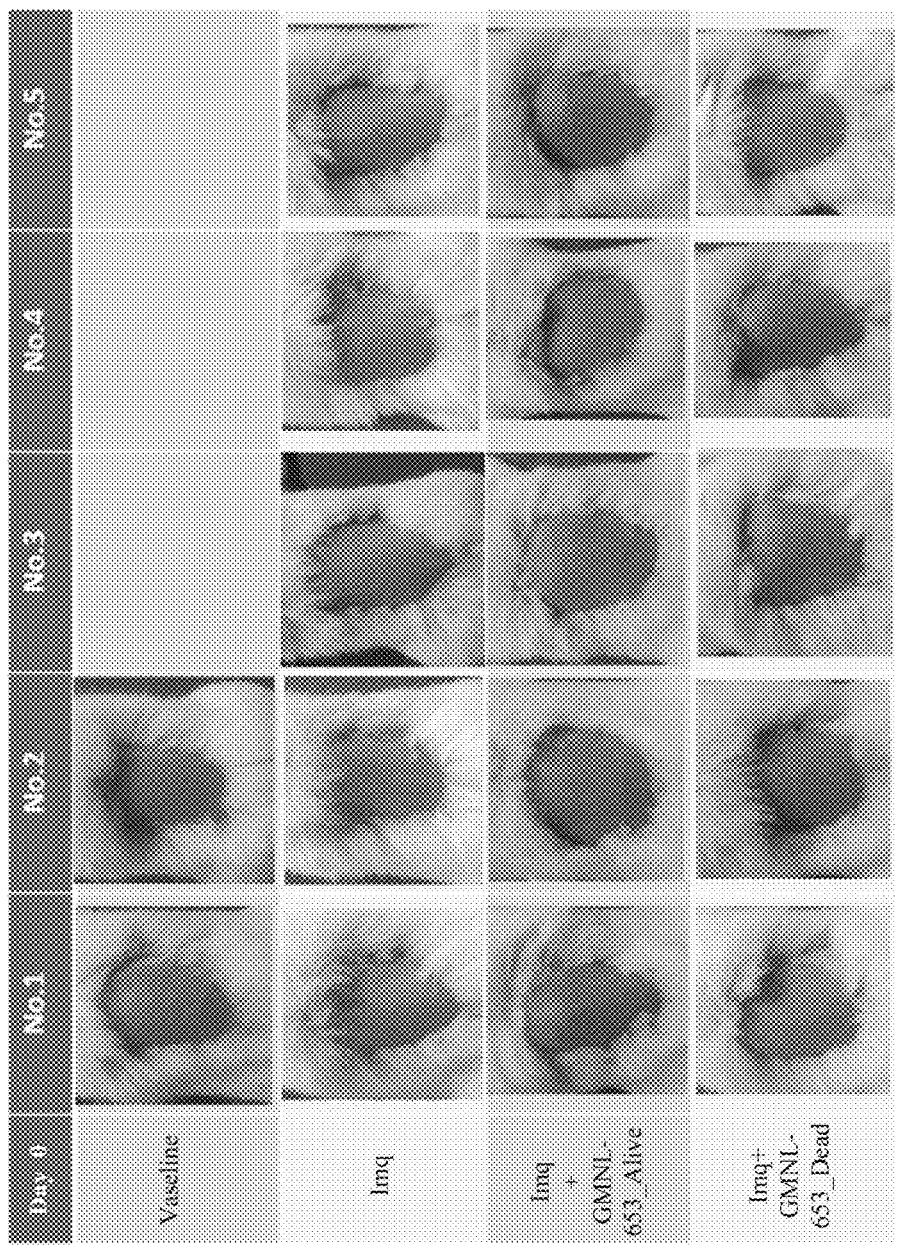
FIGS. 4A-4C are photos showing the back skin of a mouse in each group on different days.
Figure 4B:
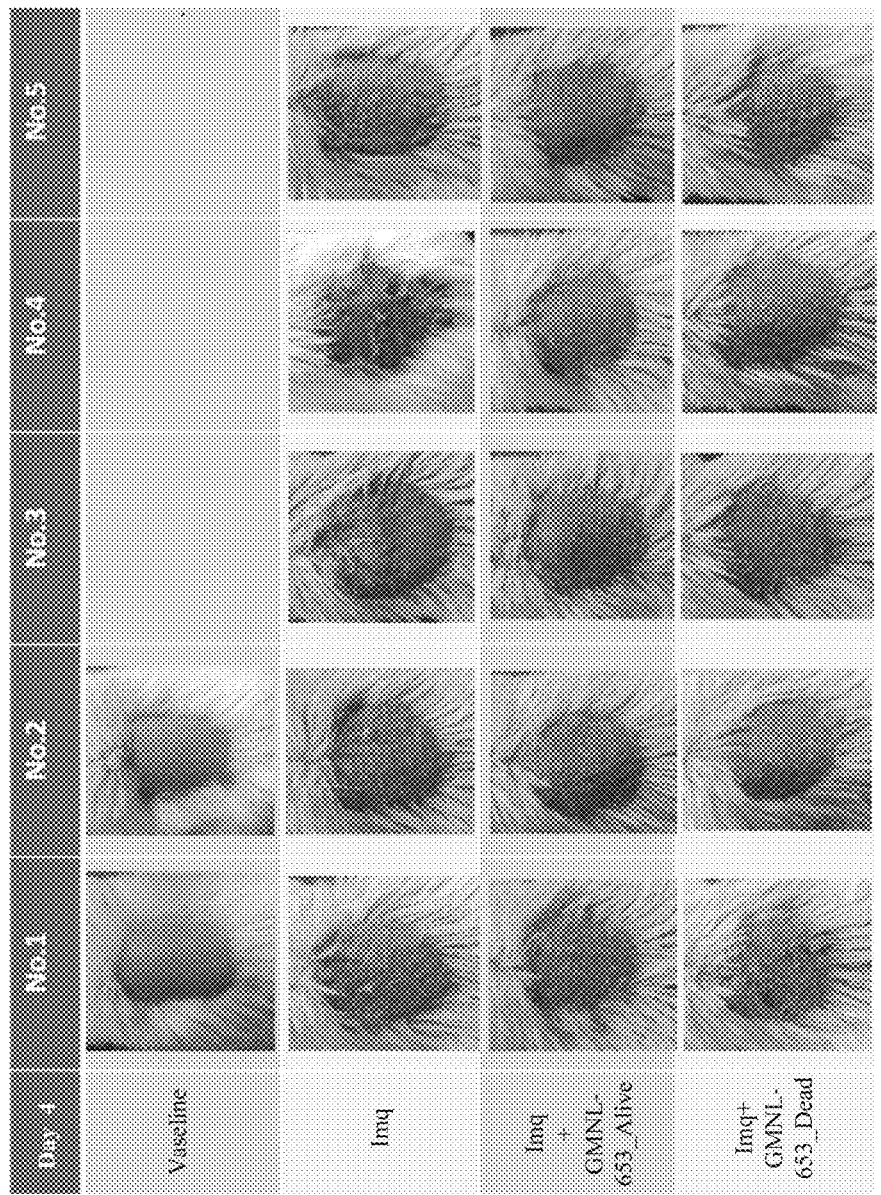
Figure 4C:
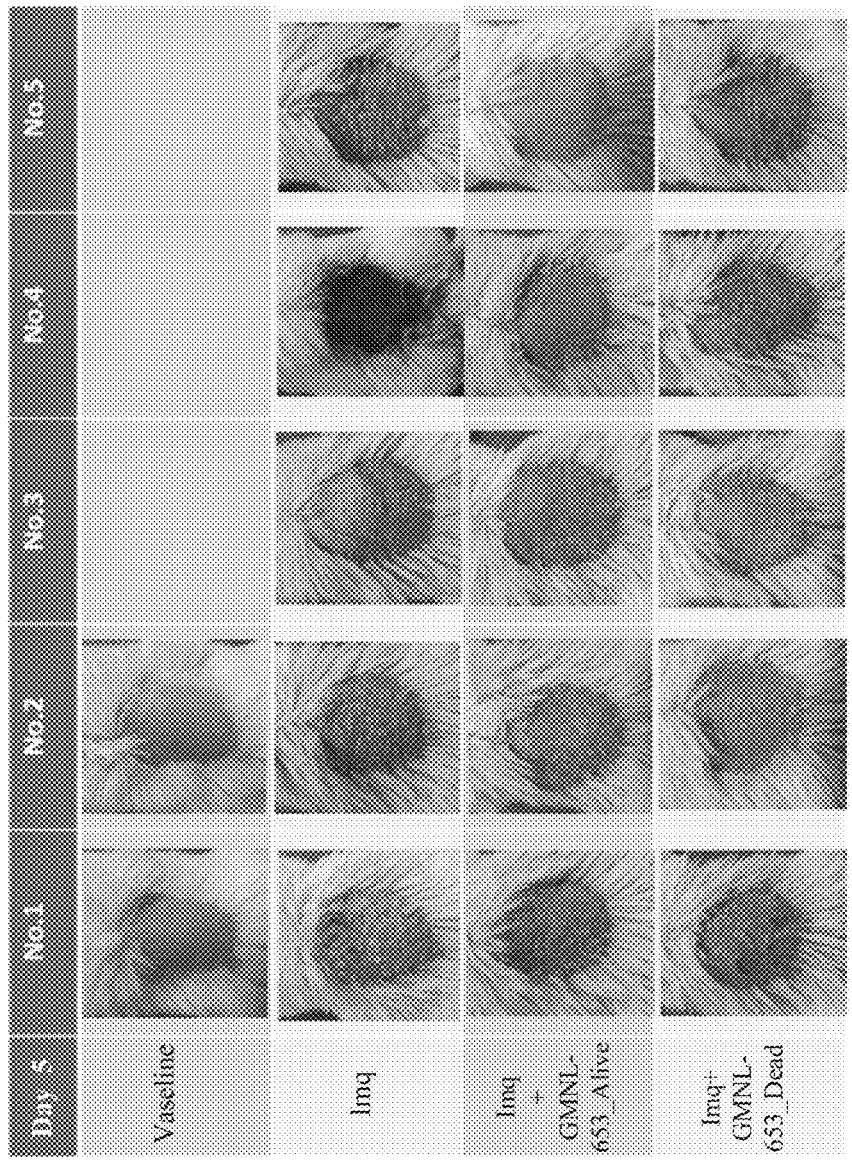

Referring to FIGS. 4A to 4C, the back skin of the mouse at the 0, 4th, and 5th day are shown, respectively. After treating with Imq cream for 4 or 5 days, the disease group (Imq) and control group (Vaseline) show significantly different conditions on the back skin. The disease group shows symptoms similar to human psoriasis, such as uplift red desquamation plaque and falling dander. In addition, there is also a wound. Compared with the Imq group, in the viable GMNL-653 and the dead GMNL-653, although the skin still forms a small amount of dander, but the parts and quantity of the uplift desquamation plaque are much reduced. That is, no matter if the stains GMNL-653 are viable or dead, the psoriasis symptoms caused by Imq can be improved/relieved greatly.

Figure 5:
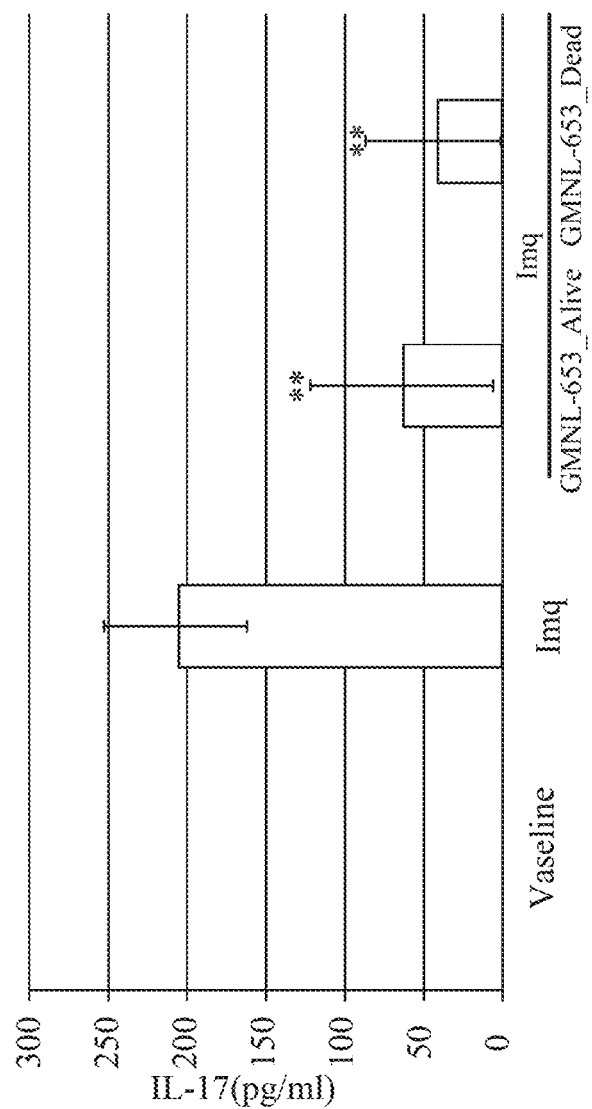
FIG. 5 is a diagram showing the effect of the *Lactobacillus paracasei* strain GMNL-653 on the cytokine IL-17 in serum in the experiment 3.
Figure 6:
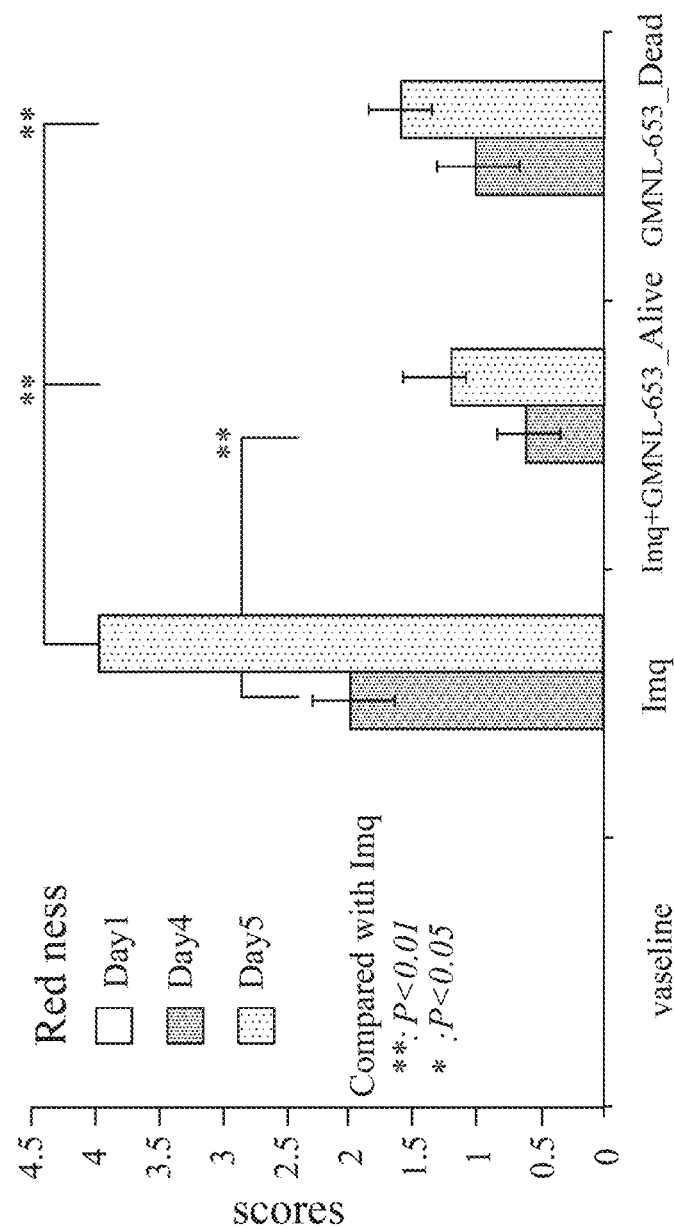
FIG. 6 shows the comparison scores obtained by evaluating the appearance of the mouse skin according to the literature method after the mouse has psoriasis.

Referring to FIG. 5, it can be seen that the cytokine IL-17 can be greatly reduced by feeding the dead GMNL-653 or the viable GMNL-653 to the mouse having the disease caused by Imq. Therefore, it can be inferred that the *Lactobacillus paracasei* strain GMNL-653 can improve/relieve the systemic inflammation caused by psoriasis through reducing the cytokine IL-17 secretion FIG. 6 is a diagram showing the comparison scores obtained by evaluating the appearance of the mouse skin according to a literature method (Bangladesh J Pharmacol. 2016; 11: 849-851) after the mouse has psoriasis. From FIG. 6, it can be found that there are no differences in the Vaseline group at day 1, 4, and 5. After the disease model is successfully constructed, all groups in which the Imq was applied had inflammatory skin irritation. However, compared with the Imq disease group, the Imq+viable GMNL-653 group and the Imq+dead GMNL-653 group both slow down the inflammatory degree of redness. The viable GMNL-653 group or the dead GMNL-653 group both have significant differences when compared with the Imq disease group (**: $p<0.01$·*: $p<0.05$).

Figure 7:
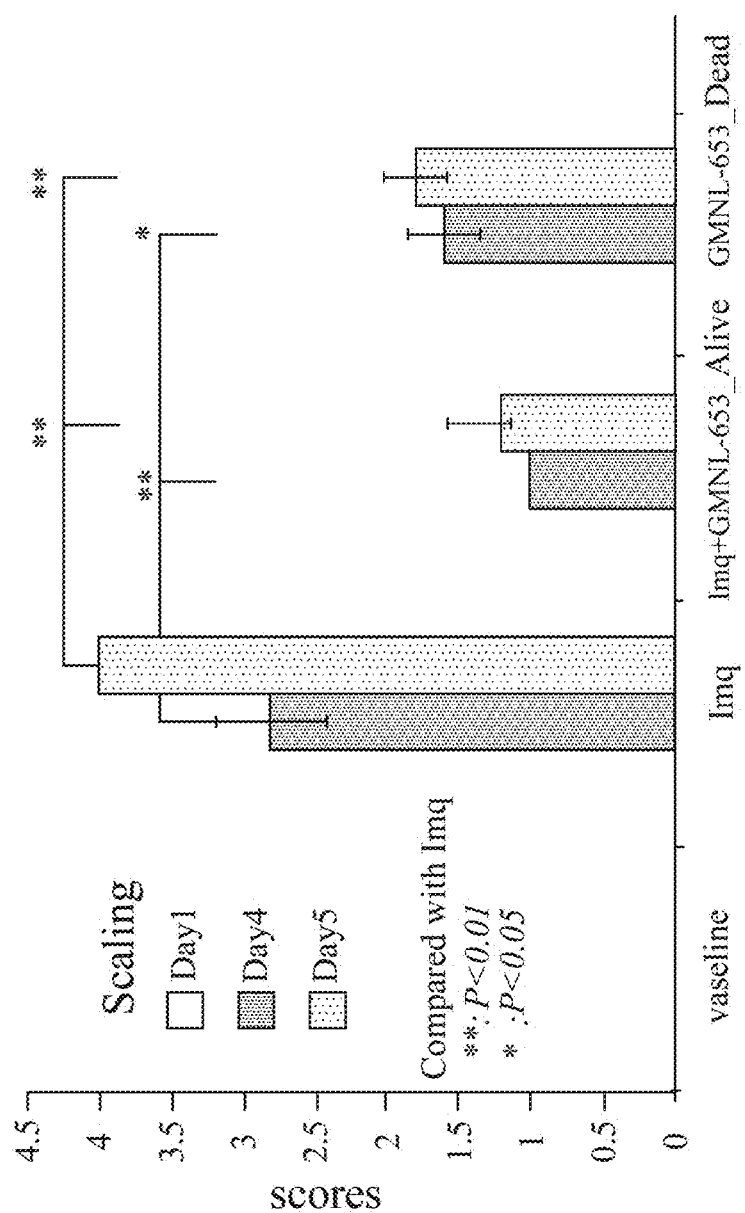
FIG. 7 shows the comparison scores obtained by evaluating the symptoms of keratosis on the mouse skin according to the literature method after the mouse has psoriasis.

FIG. 7 shows the comparison scores obtained by evaluating the symptoms of keratosis on the mouse skin according to the literature method (Bangladesh J Pharmacol. 2016; 11: 849-851) after the mouse has psoriasis. Since the stratum corneum of the skin has parakeratosis, the new dander continues to be produced and falls off of the skin. From FIG. 7, it can be seen that there are no differences in the Vaseline group at day 1, 4, and 5. After the disease model is successfully constructed, all groups in which the Imq was applied had inflammatory dander. However, compared with the Imq disease group, the Imq+viable GMNL-653 group and the Imq+dead GMNL-653 group both slow down the formation and the speed of scaling. The viable GMNL-653 group or the dead GMNL-653 group both have significant differences when compared with the Imq disease group (**: $p<0.01$·*: $p<0.05$).

In summary, according to the above results, it is certain that the *Lactobacillus paracasei* strain GMNL-653 according to the present invention, no matter if the strains are viable or dead, can significantly improve/relieve psoriasis. The mechanism of the improvement is to reduce the over-inflammation though adjusting the formation of the cytokine IL-17. The *Lactobacillus paracasei* strain GMNL-653 and the composition thereof are applicable to the treatment of psoriasis, and they are very safe, cheap, convenient to use, and have no side-effects. A deposit designation of a culture of the *Lactobacillus paracasei* GMNL-653 in the present invention was deposited in the China. Center for Type Culture Collection (CCTCC) located at Wuhan University, Wuhan 430072 P.R. China with Accession No. CCTCC M 2016226 on Apr. 25, 2016 under the Budapest Treaty.

The present invention has been described with preferred embodiments thereof and it is understood that many changes and modifications to the described embodiments can be carried out without departing from the scope and the spirit of the invention that is intended to be limited only by the appended claims.

What is claimed is:

1. A method, of treating psoriasis, comprising:
administrating to subject in need thereof, an effective amount of a composition comprising *Lactobacillus paracasei* GMNL-653 and a pharmaceutically acceptable carrier, wherein the *Lactobacillus paracasei* GMNL-653 is deposited in the China Center for Type Culture Collection (CCTCC) with an accession number of CCTCC M2016226 on 25 Apr. 2016, wherein the *Lactobacillus paracasei* GMNL-653 has an ability to inhibit the formation of cytokine IL-17 and an ability to inhibit the formation of cytokine IL-6.

2. The method according to claim 1, wherein the *Lactobacillus paracasei* GMNL-653 is a viable strain or a dead strain.

3. The method according to claim 1, wherein the composition is a pharmaceutical composition, a nutritional supplement, a health food, a medical food, or a combination thereof.

* * * * *

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: PAF primer

<400> SEQUENCE: 1
agagtttgat cctggctcag                                              20

<210> SEQ ID NO 2
<211> LENGTH: 18

```
<212> TYPE: DNA
<213> ORGANISM: Artificial Sequence
<220> FEATURE:
<223> OTHER INFORMATION: 536R primer

<400> SEQUENCE: 2
gtattaccgc ggctgctg                                                      18

<210> SEQ ID NO 3
<211> LENGTH: 523
<212> TYPE: DNA
<213> ORGANISM: Artificial Sequence
<220> FEATURE:
<223> OTHER INFORMATION: GMNL-653 16S rDNA primer

<400> SEQUENCE: 3
cggaggcccc tatgatgggc gtcgtacgag ttctcgttga tgatcggtgc ttgcaccgag       60
attctcatgg aacgagtggc ggacgggtga gtaacacgtg ggtaacctgc ccttaagtgg      120
gggataacat ttggaaacag atgctaatac cgcatagatc ctgtaaccgc atggttcttg      180
gctgatagat ggcgtaagct atcgctgttg gatggacccg cggcgtatta tctagttggt      240
gaggtagtgg ctcaccgagg ccatgatacg tatccgagct gagaggttga tgggcgagtt      300
tgtgactgag acacgtccca aactactacg ggaggcagca gtagggaatc ttccacaatg      360
gacgcaagtc tgatggagca acgccgcgtg agtgaagaag gctttcgggt cgtaaaactc      420
tgttgttgga gaagaatggt cggcagagta actgttgtcg gcgtgacggt atccaaccag      480
aaagccacgg ctaactacgt gccagcagcc gggggtaat aca                        523
```